(12) United States Patent
Shoher et al.

(10) Patent No.: US 8,119,061 B2
(45) Date of Patent: Feb. 21, 2012

(54) METHOD FOR ATTACHING METAL STRUCTURE TO A DENTAL COPING

(76) Inventors: Itzhak Shoher, Tel Aviv (IL); Aharon Whiteman, Petach-Tikvah (IL)

( * ) Notice: Subject to any disclaimer, the term of this patent is extended or adjusted under 35 U.S.C. 154(b) by 656 days.

(21) Appl. No.: 12/316,546

(22) Filed: Dec. 15, 2008

(65) Prior Publication Data

US 2009/0152330 A1 Jun. 18, 2009

Related U.S. Application Data

(62) Division of application No. 11/243,270, filed on Oct. 4, 2005, now abandoned.

(51) Int. Cl.
*B22F 3/10* (2006.01)
*B23K 31/02* (2006.01)

(52) U.S. Cl. ......... 419/8; 419/23; 228/194; 228/262.61; 433/180; 433/181

(58) Field of Classification Search ............... 419/8, 23; 228/119, 194, 262.61; 433/180, 181; 75/255; 148/24
See application file for complete search history.

(56) References Cited

U.S. PATENT DOCUMENTS

| | | | | |
|---|---|---|---|---|
| 4,704,089 A | * | 11/1987 | Shoher et al. | 433/183 |
| 4,990,394 A | * | 2/1991 | Shoher et al. | 428/212 |
| 5,074,791 A | * | 12/1991 | Shoher et al. | 433/180 |
| 5,314,109 A | * | 5/1994 | Farzin-Nia | 228/262.42 |
| 6,213,776 B1 | * | 4/2001 | Shoher et al. | 433/207 |
| 6,617,043 B2 | * | 9/2003 | Shoher et al. | 428/553 |

* cited by examiner

*Primary Examiner* — Roy King
*Assistant Examiner* — Ngoclan Mai

(57) ABSTRACT

A method for attaching a metal structure to a dental coping having opposite sides in the preparation or repair of a dental restoration comprising the steps of: (1) forming a dental material composition comprising high-fusing temperature metal particles in a range of between 1-10 weight percent with the high-fusing temperature metal particles having at least 30% thereof selected from the platinum group of metals, low fusing temperature metal particles having a melting temperature below the melting temperature of the high-fusing particles with the low fusing temperature metal particles being present above at least about 90 weight percent of the total composition and being composed primarily of gold, and a small measure of borate fluxes in a range of between 0.1 to 2.0% by weight of the total composition; (2) adding a volatile binder such that the dental material composition forms a loose paste; (3) placing paste between the metal structure and the metal coping; and (4) applying heat to the dental material composition at a temperature below the melting temperature of the high-fusing temperature metal particles and at or above the melting temperature of the low-fusing temperature metal particles to cause the dental material composition to solidify into a relatively dense solid.

8 Claims, 2 Drawing Sheets ially of gold. The high fusing temperature
METHOD FOR ATTACHING METAL STRUCTURE TO A DENTAL COPING This application is a division of application Ser. No. 11/243,270, filed on Oct. 4, 2005, now abandoned.

FIELD OF THE INVENTION

This invention relates to a dental material for attaching a cast metal structure to a dental coping for preparing and/or repairing a dental restoration.

BACKGROUND OF THE INVENTION

In crown and bridge prosthodontics, metal copings are conventionally used to provide the essential structural strength and rigidity necessary for a dental restoration to resist the forces of mastication. In a ceramic-to-metal dental restoration, the metal coping represents the retaining member which forms the understructure of the restoration in the preparation of a single or multiple unit bridge. A bridge is used to replace at least one missing tooth and is supported by one or more natural teeth. The bridge includes a pontic which fills the edentulous space represented by the missing tooth and a connector which serves to connect the pontic to a retaining member formed on an abutment tooth adjacent the pontic. The bridge may be a single unit bridge involving the preparation of one or two retaining members or a multiple unit bridge. The pontic is formed from a model of the missing tooth and is typically of cast metal. The connector is typically a soldered joint extending between the cast metal structure and the coping.

For purposes of the present invention any conventional method may be used to form the dental metal coping and any conventional method may be used to form the metal structure although a cast structure is preferred. The dental metal composition of the present invention forms a soldered connection between a dental coping composed of precious metals and a metal structure composed entirely or substantially of precious metals.

The soldered joint formed between the metal coping and metal structure should result in a strong rigid prosthetic structure without voids or gaps which would otherwise provide space for the growth of bacteria. Moreover, the soldering operation should not result in excessive shrinkage of the metal composition during heat treatment to preserve the physical and spatial relationship between the coping and the cast metal structure that existed before heat treatment and without causing oxidation.

SUMMARY OF THE INVENTION

The dental material composition of the present invention comprises a minority of high-fusing temperature metal particles in a range of between 1-10 weight percent, a majority of low fusing temperature metal particles having a melting temperature below the melting temperature of the high-fusing particles and a small measure of borate fluxes in a range of between 0.1 to 2.0% by weight of the total composition, with the low fusing metal component in excess of at least 90 wt % preferably at least 95 wt % of the total composition and composed primarily of gold. The high fusing temperature metal particles are preferably non-spherical in shape whereas the shape of the low fusing temperature metal particles are preferably spherical in shape.

BRIEF DESCRIPTION OF THE DRAWINGS

Additional advantages of the present invention will become apparent from the following detailed description of the invention when read in conjunction with the accompanying drawings of which.

DETAILED DESCRIPTION OF THE INVENTION

The dental material composition of the present invention includes a component of high-fusing temperature metal particles of up to no more than about 10 weight percent, a component of low fusing temperature metal particles, a small measure of one or more borate fluxes and a volatile binder preferably in liquid form. The melting temperature of the high fusing component may be as low as 1075° C. but is preferably above 1100° C. whereas the low-fusing temperature metal particles must have a melting temperature below that of the melting temperature of the high-fusing metal particles.

The component of high-fusing temperature metal particles is a composition of precious metals composed of at least 30% of metals selected from the platinum group of elements, primarily of platinum and palladium as well as other minor additional constituents such as Ag, Cu, Mg, Al, Zn. Other metals of the platinum group of elements may be included from the third and fourth group of elements. The total weight percent of the high fusing component should not exceed ten weight percent of the total material composition and should preferably be in a range of between 1-10 weight percent of the total dental material composition and optimally in a range of between 3-6 wt %. In addition, the high-fusing temperature metal particles should be of a size less than about 30 microns when measured by sieving and should have an irregular non-spherical shape preferably in the form of thin platelet like flakes.

The low-fusing temperature metal component should be in the form of particles composed preferably of gold or a gold alloy such as gold and silver with gold as the major constituent, optimally with gold in excess of at least 90% and preferably in excess of 95 wt % of the low-fusing temperature metal component and optimally at least 97 wt % of the low-fusing temperature metal component. The preference for gold as the major constituent of the low-fusing component is based on its known characteristics of workability, biocompatibility, non-oxidizing properties, and color. The low-fusing temperature metal particles should preferably be spherical in shape and of less than 10 microns in diameter.

The low-fusing temperature metal component should be equal to or in excess of 90 weight percent of the total dental material composition with the particles of low high-fusing temperature metal less than about 10 microns in size when measured by sieving and may be of any shape but preferably spherical.

Borate fluxes should be included in the dental metal composition in a range of between 0.1-2.0% of the total weight composition and preferably between 0.7 and 1.3 weight percent.

A volatile binder is added to the dental material composition to form a paste. A liquid binder is preferred such as alcohol and water or any other organic compound such as ethylene glygol. However any binder composition may be used which will vaporize during heat treatment including a non-liquid wax.

Figure 1:
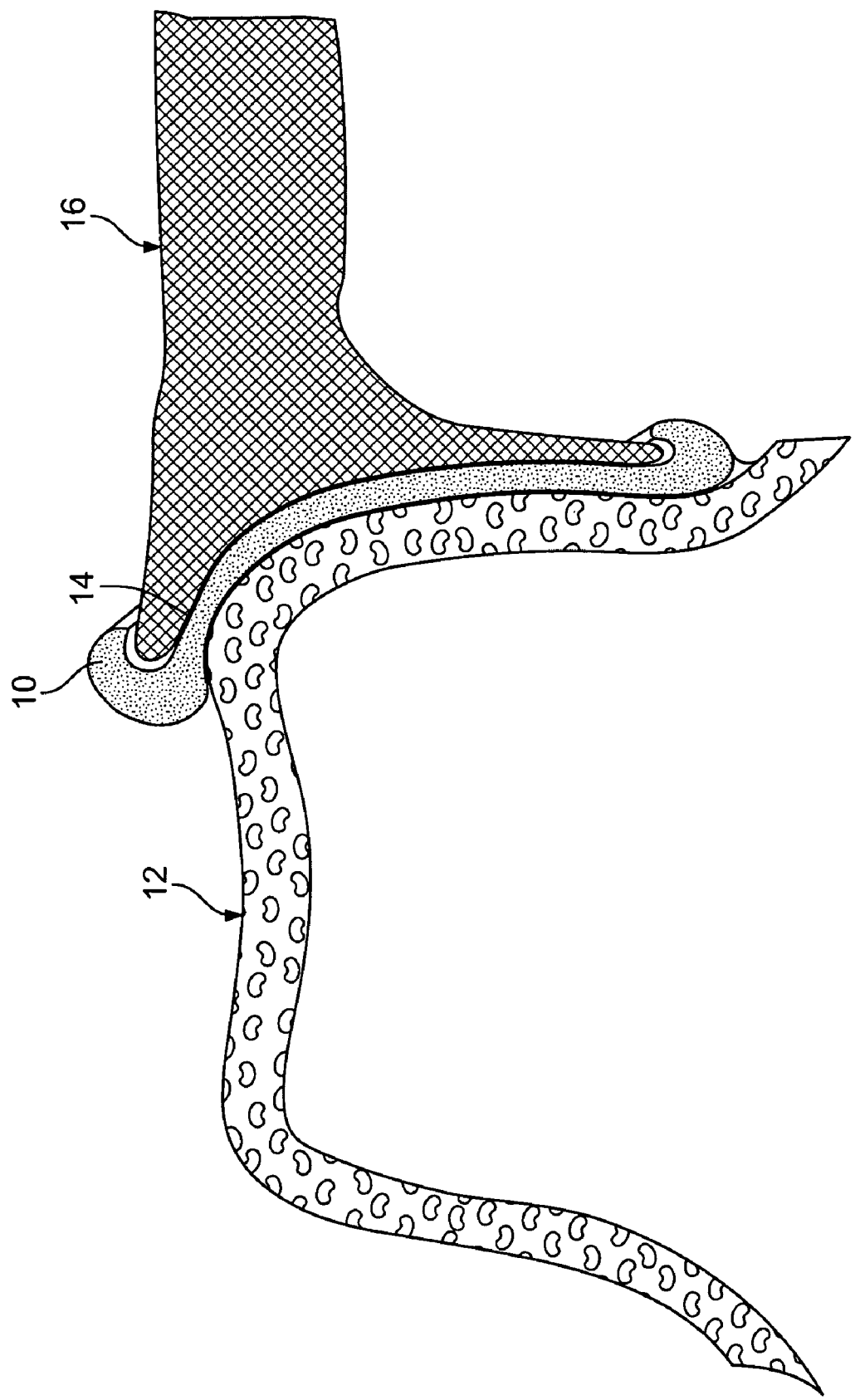
FIG. 1 is a cross sectional view of a metal coping coupled to to one end of a metal cast structure using the dental material composition of the present invention before the application of heat treatment.

Sufficient binder is added to the composition to form a mixture in the form of a loose paste. The loose paste of the dental material composition 10 is placed on adjacent surfaces between the metal coping 12 and the adjacent end 14 of the cast metal structure 16 which is only partially shown in FIG. 1. The cast metal structure 16 may be placed over the coping 12 or along side it with one pressed against the other to push the composition of paste binder 10 into intimate contact to fill the gap between the coping 12 and the end 14 of the cast metal structure. Additional paste may be added as needed at the edges between the end 14 of the cast and the coping 12 so that no space exists.

Heat is applied to the dental material composition from any heat source including a flame or by placement of the joined parts in a dental furnace at a temperature below the melting temperature of the high fusing temperature metal particles and at or above the melting temperature of the low fusing temperature metal particles for a short interval of time typically between 1-3 minutes. A preferred heat treatment temperature is about 1050° C.

Figure 2:
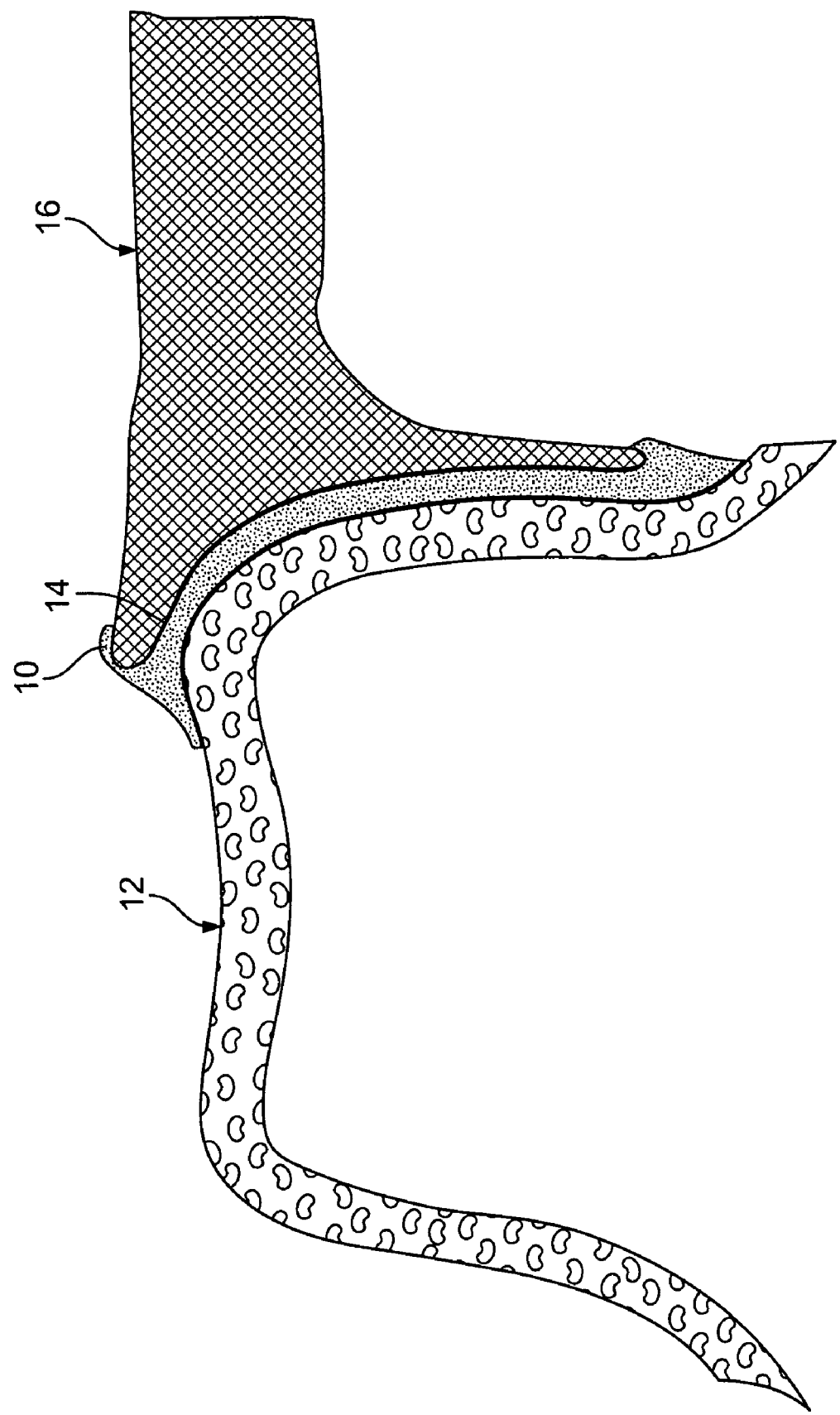
FIG. 2 is a similar cross sectional view the metal coping and metal cast structure of FIG. 1 shown after heat treatment.

The material composition after heat treatment solidifies as shown in FIG. 2 into a relatively dense solid so as to provide sufficient structural integrity to withstand normal biting forces.

What is claimed:

1. A method for attaching a metal structure to a dental coping having opposite sides in the preparation or repair of a dental restoration comprising the steps of: (1) forming a dental material composition comprising high-fusing temperature metal particles in a range of between 1-10 weight percent with the high-fusing temperature metal particles having at least 30% thereof selected from the platinum group of metals, low fusing temperature metal particles having a melting temperature below the melting temperature of the high-fusing particles with the low fusing temperature metal particles being present above at least about 90 weight percent of the total composition and being composed primarily of gold, and a small measure of borate fluxes in a range of between 0.1 to 2.0% by weight of the total composition; (2) adding a volatile binder such that the dental material composition forms a loose paste; (3) placing the metal structure against one side of the metal coping to which it is to be attached with the loose paste of dental material composition inserted between the one side of the metal coping and the metal structure; and (4) applying heat to the dental material composition at a temperature below the melting temperature of the high-fusing temperature metal particles and at or above the melting temperature of the low-fusing temperature metal particles to cause the dental material composition to solidify into a relatively dense solid.

2. A method as defined in claim 1 wherein the low fusing temperature metal particles is present above at least 95 wt % of the total composition.

3. A method as defined in claim 2 wherein the high fusing temperature metal particles are preferably non-spherical in shape.

4. A method as defined in claim 3 wherein the high fusing temperature metal particles are less than 30 microns in size.

5. A method as defined in claim 4 wherein the high fusing temperature metal particles are in a range of between 3-6 weight percent.

6. A method as defined in claim 5 wherein the low fusing temperature metal particles are preferably spherical in shape.

7. A method as defined in claim 6 wherein the low fusing temperature metal particles are composed of at least 97 wt % gold.

8. A method as defined in claim 7 wherein said volatile binder is a liquid of water and an organic compound.

* * * * *